United States Patent [19]

Delhaye et al.

[11] 4,030,827

[45] June 21, 1977

[54] APPARATUS FOR THE NON-DESTRUCTIVE EXAMINATION OF HETEROGENEOUS SAMPLES

[75] Inventors: Michel Delhaye, Villeneuve D'Ascq; Yves J. M. Moschetto, Haubourdin; Paul Dhamelincourt, Villeneuve D'Ascq, all of France

[73] Assignee: Institut National de la Sante et de la Recherche Medicale (Inserm), Paris, France

[22] Filed: Dec. 2, 1974

[21] Appl. No.: 528,804

[30] Foreign Application Priority Data

Dec. 3, 1973  France .................... 73.42945

[52] U.S. Cl. .................... 356/75; 356/85
[51] Int. Cl.² .......................... G01J 3/44
[58] Field of Search ................. 356/75, 85

[56] References Cited

UNITED STATES PATENTS

| 3,802,777 | 4/1974 | Regnier et al. ............ 356/75 |
| 3,832,558 | 8/1974 | Fern et al. ............... 356/85 |

OTHER PUBLICATIONS

"Analytical . . . Chemical Processes," Fowler et al., IBM Tech. Disc. Bulletin, vol. 15, No. 12, May, 1973, pp. 3885–3886.

"Raman . . Insolid State Physics," Shepherd, Applied Optics, vol. 11, No. 9, Sept., 1972, pp. 1924–1927.

*Primary Examiner*—Vincent P. McGraw
*Attorney, Agent, or Firm*—Robert B. Frailey

[57] ABSTRACT

The present invention relates to an apparatus for the non-destructive examination of an heterogeneous sample by analysis of the Raman radiations scattered by the sample receiving an incident of monochromatic radiation of known frequency. The apparatus includes a source of monochromatic light, such as a laser beam, a monochromator for selecting and measuring the change in frequency of the Raman scattered or re-emitted radiations with respect to the frequency of the incident radiation, a radiation detector and an amplifier to amplify signals from the detector. The apparatus identifies each such re-emitted radiation by comparison with control samples or reference spectra. The invention enables selective mapping of the distribution of the polyatomic ions, crystals and molecules of the sample. Apparatus embodying the invention permits mapping, by micrographic images, of the components of geological samples, composite materials, plastic materials, biological samples, microscopic preparations and the like, by isolating in the Raman spectrum the radiations characterizing the components.

6 Claims, 2 Drawing Figures

APPARATUS FOR THE NON-DESTRUCTIVE EXAMINATION OF HETEROGENEOUS SAMPLES

BACKGROUND OF THE INVENTION

The present invention relates to a device for the non-destructive examination of heterogeneous samples by analysis of the Raman radiations scatter by said samples.

The study of heterogeneous samples is a constant source of interest of the physicist or technician seeking to discover the nature and structure of certain bodies. Examination is already effected by the microscope, in particular the electronic probing by the spectroscopy of emissions by lasers. However, facilities are never sufficient for the research worker.

The device according to the invention provides a new way of studying bodies by using light scattering physical-phenomena known as the Raman effect.

Microscopy is already known where the photons of a radiation are sent onto a substance. This radiation is then absorbed and converted and it is re-emitted at a higher wave length that may be analysed under a microscope and which reflects the nature of the surface studied. The microscope used is sensitive to the re-emitted light at its wave length of re-emission. However, examination by this microscope often needs to be completed by another examination.

Electronic micro-probing is also known, which has been hinted at above. This process permits only a very local observation of the matter.

Radiation is also known, produced by a light amplifier by stimulated emission of electromagnetic radiation which produces a high intensity light source of coherent light, called a "laser". Laser radiation has been applied to a process of studing surfaces, which consists in sending its radiation so that it vaporises the substance, of which the vapours may be analysed by spectroscopy.

The drawback of this process is that it destroys the matter, at least locally.

Electronic scanning techniques are also known, which are widely used in television. Instead of scanning a fixed surface by a rapidly moving beam of radiations, the beam may also be fixed and the surface to be explored may move along the abscissa and, by shifting slightly each time, along the ordinates, to effect a similar scanning.

In optics, slotted monochromators are also known which select the radiation received and furnish a monochromatic radiation. Radiation detectors are also known which may be of the photomultiplier type to be able to obtain signals that may be amplified by the known electronic techniques, particularly for cathode tubes restoring a visible image directly or to constitute recordings which may be used subsequently. Laser Raman spectroscopy, utilizing Raman scattering for the qualitative and quantitative chemical analysis of samples, also is known. Raman spectrometers have proven to be valuable laboratory tools for identifying and recording Raman spectra in connection with the investigation of the molecular properties of matter.

SUMMARY OF THE INVENTION

The present invention utilizes these different elements in order to produce a novel device for examining samples and selectively mapping the distribution of their polyatomic structures.

The apparatus of the invention is characterized in that, utilizing the Raman effect to analyze a sample, it includes means to identify each polyatomic component of the sample by isolating in the Raman spectrum the Raman line or radiation characterizing each such component. An incident monochromatic radiation is furnished from a light source by a conventional emitter having capacity to select with accuracy its wave length or frequency, nature and intensity, to ensure that the power of the light does not exceed the threshold of destruction of the surface of the sample. Conventional means are provided for selecting and measuring the change in frequencies of the Raman radiations re-emitted or scattered by the sample with respect to the frequency of the incident monochromatic radiation. The Raman scattered radiations represent the structure of the sample. A conventional radiationdetector detects the Raman radiation selected, and an amplifier amplifies signals from the detector. Where the components of the sample are unknown, their identity may be ascertained by comparison of the Raman results obtained with results from known samples or with reference spectra. Finally, novel means are provided for selectively mapping the components of a sample by the production of micrographic images of the shape, position and distribution of its polyatomic structures utilizing the information obtained from the Raman scattered light provided by the sample.

Generally, the incident radiation will be constitued by a low power laser beam which may,
- either cover all the surface of the sample examined and the re-emitted radiation is treated to give an overall image thereof, similar to the one obtained in microscopy,
- or be concentrated at spots on the surface to be studied and it scans it systematically to re-emit a radiation which is detected and amplified in order to be studied.

DESCRIPTION OF THE FIGURES OF THE DRAWING

The invention will be more readily understood on reading the following description with reference to the accompanying drawings, in which.

DETAILED DESCRIPTION OF THE INVENTION

Figure 1:
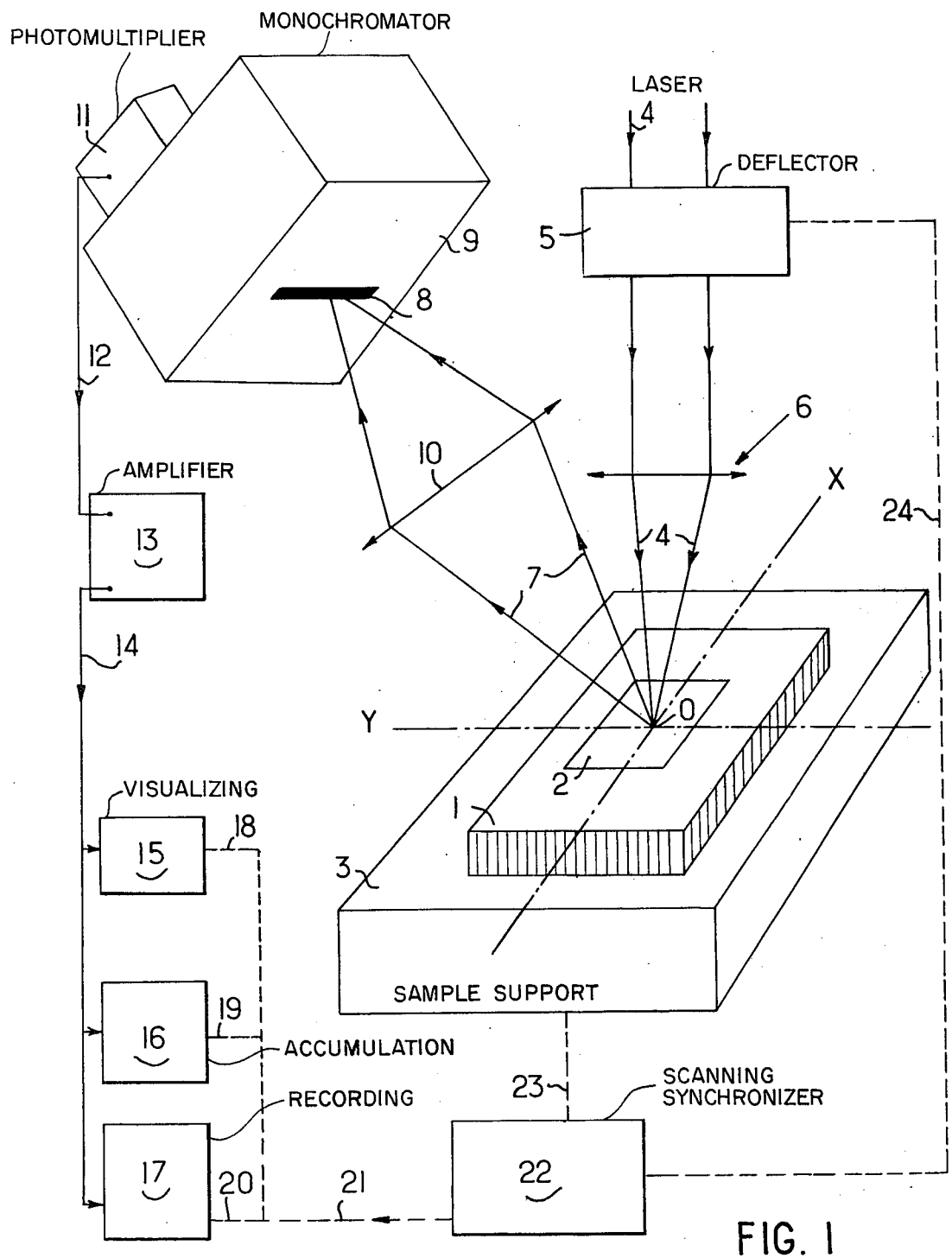
FIG. 1 is a schematic view showing the whole of the device using the scanning technique.

Referring now to the drawings, the device shown in FIG. 1 makes it possible to study a sample 1, at least in its exploration zone 2 which has been shown to be rectangular, so that it is scanned in the direction of the X-axis (abscissa) and in the direction of the Y-axis (ordinates). The scanning may be entirely electronic in the two directions or be simply linear, parallel to the X-axis. In this latter case, the mechanism 3 supporting the sample 1 comprises a device for displacement along the Y-axis so that several lines parallel to the X-axis may be explored. The mechanism 3 presents positioning means constituted by usual devices (not shown) for the sample 1 and usual devices (not shown) for orientation and displacement along the X-axis annd Y-axis.

The sample 1 receives a radiation, generally a monochromatic laser beam shown by arrows 4, which may be deflected in the direction of the X-axis by the optical deflector 5 then focussed by lens assembly 6 to be concentrated at point 0.

The matter at point 0 re-emits or scatters another radiation, shown by arrows 7, which is of different wave length from that of the incident light or beam 4. As was indicated hereinbefore, this phenomen is known and has already been demonstrated in the phenomen of fluorescence, the Raman effect, the Brillouin effect or even, the case of internal movement in the matter of which the sample is composed, by the Doppler-Fizeau effect. In fact, it is specified that the device of the invention makes it possible to study samples 1 of any nature, whether they be solid, liquid, or gaseous. The sample 1 may, moreover, be contained in any container, preferably transparent, so that it can be studied not only in the open air, but also in a controlled atmosphere or in vacuo. The scattered or re-emitted light or radiation 7 is focussed on the slit 8 of the monochromator 9, by allens assembly 10, preferably a wide aperture lens. As explained previously, the device employs the Raman effect in the practice of the invention. The re-emitted radiation 7 which the invention utilizes is the Raman scatter light focused by the lens 10 on the entrance slit 8 of the monochromator 9. The monochromator 9 receives the Raman scattering from the sample 1, permits the determination of the differences between the frequencies of the Raman scattered radiations and the frequency of the incident radiation 4, and selects and transmits one of the scattered or re-emitted Raman radiations to a photomultiplier 11.

The radiation is then detected by the photomultiplier 11 which transforms it into electrical signals which are sent via line 12 towards an amplifier 13 which, itself, via line 14, sends amplified signals simultaneously or separately towards a known visualising device 15, accumulation device 16 and recording device 17. Respective lines 18, 19 and 20 receive signals coming from the line 21 connected to the scanning synchroniser 22 which also sends signals to the mechanism 3 via line 23, when the sample must be moved slightly along the Y-axis, and to the optical deflector 5 via line 24 to carry out scanning along the X-axis.

The operation of the device described up to the present and illustrated in FIG. 1, has been explained in the course of this description. However, it may further be specified that the incident beam 4, which will generally be a laser beam, will be chosen with the best wave length compatible with the study of the sample 1. This selection of the wave length of the incident beam 4 may be effected by selective optical filters, a tunable filter or another other device enabling the same result to be achieved.

Similarly, the re-emitted radiation is also studied by selective optical filters which are specially made for each of the components contained in the sample, or by a tunable filter or by an adjustable monochromator, these devices forming part, in FIG. 1, of the whole, which is generally referenced by 9.

As a function of this, the device may be used, either in excitation at fixed wave length and, in this case, the Raman scattering 7 is analysed with the adjustable devices including in the reference 9 indicated as "monochromator", or in excitation at variable wave lengths, the observation of the Raman scattering being effected in such case, at constant wave length and each component being characterised by the choice of the wave length of the radiation emitted by the laser.

Figure 2:
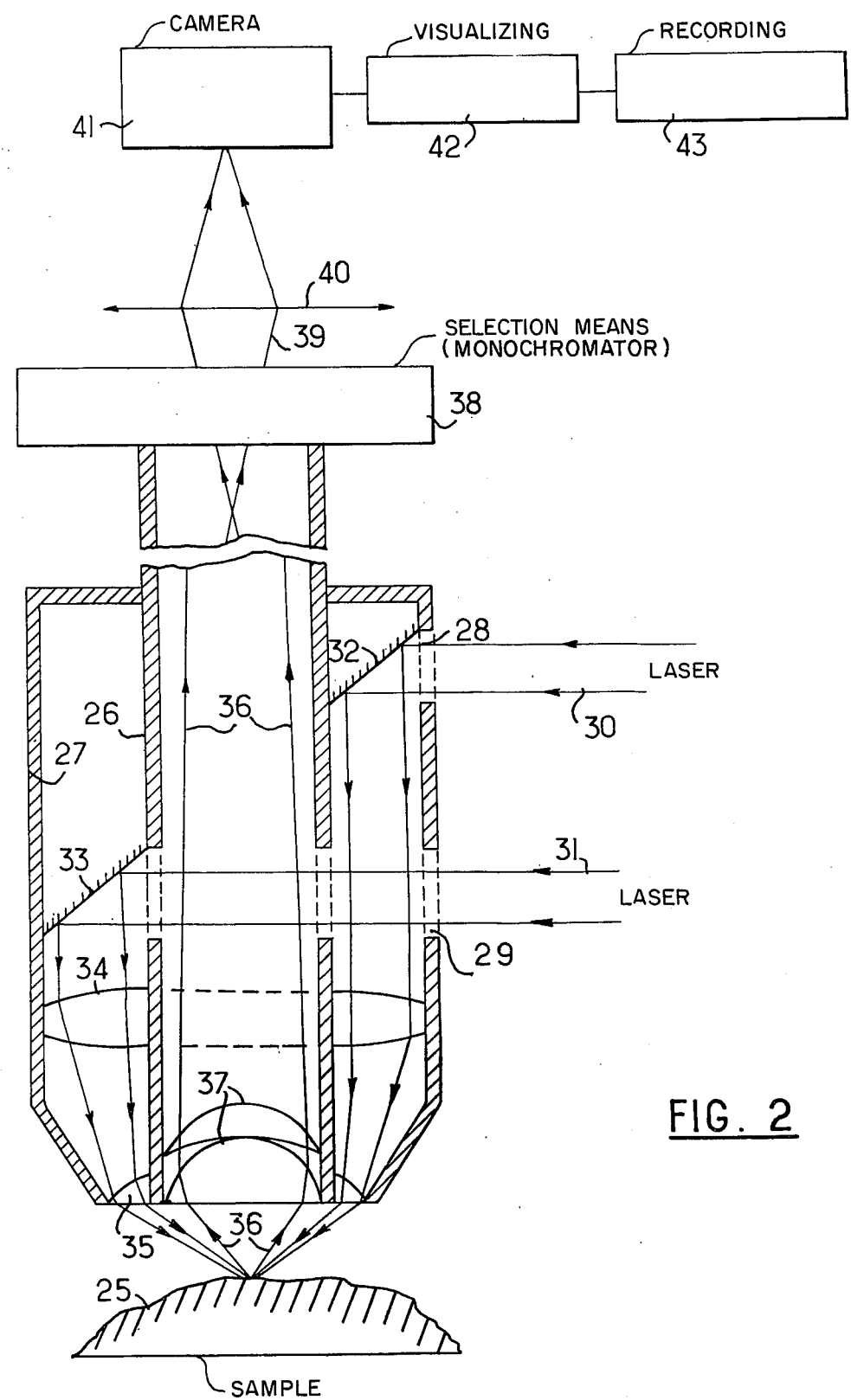
FIG. 2 is a schematic view of a device without scanning.

In the embodiment of FIG. 2, the sample 25, supported by a suitable mechanism (not shown) receives a radiation, and is observed in its totality. To this end, a device is provided which is schematized by a central tube 26 and an outer tube 27, concentric therewith. The tube 27 has openings 28, 29 which make it possible laterally to receive an incident beam 30, 31 which is returned into the axis of the tube 27 by the reflecting surfaces 32, 33 and focussed by lenses 34, 35, on the sample 25. In fact, focussing is effected in similar manner to what happens in an optical microscope where an episcopic zone of the sample is illuminated.

According to the physical principles indicated hereinbefore, a Raman scattered radiation 36 is produced which is picked up by a lens assembly 37 which focuses said radiation 36 in the axis of the tube 26 towards the selection means 38 which is an optical filter that may be a monochromator. The radiation 39 which leaves the selection means 38 is orientated by an optical device 40 and examined by a camera 41. Camera is understood to mean a photographic, cinematographic or television camera which are able to observe low intensity radiations. It will be suitable to use a television camera for low level signals which will send these signals to a visualizing device 42 and, to a recording device 43.

With this device, a magnified image of the surface is observed through optical filters of which the pass bands are centered on frequencies characteristic of the Raman spectra of each of the components of the sample. When the visual observation thereof cannot be effected directly, it can be recorded. This latter device, not requiring the focussing of the laser beam, appears to be better adapted to a high-magnification microscopic study and will not risk damaging the sample.

The two devices described are not limiting and a mixed device may for example be imagined in which the laser illuminates a line of the surface of the sample. The image of this line is projected through a monochromator onto a photographic or photoelectric radiation receiver, such as an image intensifier tube followed by a memory tube camera, for example. The sample is scanned by displacement of the line observed either by the samples being moved, or by optical deflection, this displacement being effected in synchronism with the line recording device.

All these devices may be used in a manner similar to what has been indicated hereinabove with reference to the description of the operation of the first embodiment of the device, namely in excitation at fixed wave length or in excitation at variable wave length.

This apparatus has numerous examples of application as far as the studies of geological samples, composite material, plastics material, biological samples or even gas are concerned. Compared with the electronic and ionic miro-probes, which study the samples in vacuo and detect traces due to atomic properties, the present device functioning with the laser makes it possible to study samples in the open air or in controlled atmosphere. It detects the components of a heterogeneous sample by their molecular properties by isolating in the Ramam spectrum those radiations characterizing each component. This device is therefore not indicated for the detection of traces, but, on the other hand, it is suitable for the study of composite crystals (in geology, mineralogy or metallography, for example), of semiconductors (such as integrated circuits), of organic compounds (such as plastics materials), or pharmaceutical or biological products, microscopic sections and preparations, for example. The apparatus of this invention permits the selective mapping of the distribution of the polyatomic ions, crystals and molecules of which a sample is composed. By means of the invention, it is possible to obtain very good images and micrographs of the components in a heterogeneous sample, by utilizing the Raman frequency characterizing each component. The invention permits the production of micrographic images showing not only the distribution, but also the shape and position, of the polyatomic components in a sample. The invention, therefore, provides a novel and unique way to map the "geography" of the polyatomic components of a heterogeneous sample.

Although preferred embodiments of this invention have been shown and described for the purpose of illustration, it is to be understood that various changes and modifications may be made therein, without departing from the spirit and utility of the invention, or the scope thereof as set forth in the claims. For example, while the invention has been designed specifically for use in the study and examination of heterogeneous samples, it will be understood that the invention also is useful for the examination of homogeneous samples.

What is claimed is:

1. Apparatus utilizing the Raman effect for the production of micrographic images of the polyatomic components of a sample, comprising:
   a. a selectively moveable support for the sample,
   b. a source of monochromatic radiation,
   c. means permitting the non-destructive illumination of all or part of the sample by the monochromatic radiation,
   d. optical means for converging Raman radiations scattered by the sample in the direction of a monochromator,
   e. a monochromator for receiving the Raman radiations scattered by the sample, permitting the determination of the differences between the frequencies of the scattered radiations and the frequency of the monochromatic radiation, and selecting and transmitting one of the Raman radiations,
   f. photoelectric means for detecting the Raman radiation transmitted by the monochromator and
   g. means for the production of micrographic images of the shape, position and distribution of the polyatomic components of the sample utilizing information furnished by the photoelectric detection means.

2. The apparatus as defined in claim 1, wherein
   a. the means permitting the illumination of the sample scans along a line on the sample under the control of a scanning synchronizer,
   b. the support for the sample and the means permitting the illumination of the sample are moveable relative to each other in a direction perpendicular to the line of scanning under the control of the scanning synchronizer,
   c. the photoelectric detection means comprises a photomultiplier and
   d. the means for producing the micrographic images receives signals from both the photomultiplier and the scanning synchronizer.

3. Apparatus as defined in claim 1, wherein
   a. the means permitting the illumination of the sample illuminates a complete line of the sample,
   b. the support for the sample and the means permitting the illumination of the sample are moveable relative to each other under the control of a scanning synchronizer and
   c. the means for producing the micrographic images receives signals from both the photoelectric means and the scanning synchronizer.

4. Apparatus as defined in claim 1, wherein the monochromatic radiation is a low power laser beam.

5. Apparatus utilizing the Raman effect for the production of micrographic images of the polyatomic components of a sample, comprising:
   a. a selectively moveable support for the sample,
   b. a source of monochromatic radiation,
   c. means permitting the non-destructive illumination of at least part of the sample by the monochromatic radiation,
   d. optimal means comprising a microscope for converging Raman radiations scattered by the sample in the direction of a monochromator,
   e. a monochromator for receiving the Raman radiations scattered by the sample, permitting the determination of the differences between the frequencies of the scattered radiations and the frequency of the monochromatic radiation, and selecting and transmitting one of the Raman radiations
   f. and means including a camera for detecting and producing micrographic images of the shape, position and distribution of the polyatomic components of the sample.

6. Apparatus as defined in claim 5, wherein
   a. the monochromatic radiation is a low power laser beam and
   b. the camera is of the type having capacity to detect low intensity radiations.

* * * * *

UNITED STATES PATENT OFFICE
CERTIFICATE OF CORRECTION

PATENT NO. : 4,030,827
DATED : June 21, 1977
INVENTOR(S) : Michel Delhaye et al

It is certified that error appears in the above-identified patent and that said Letters Patent are hereby corrected as shown below:

Column 1, line 36  change "studing" to --studying--

Column 1, line 57  change "Ram an" to --Raman--

Column 2, line 17  change "radiationdetector" to --radiation detector"

Column 2, line 35  after "surface" insert --of the sample--

Column 2, line 65  change "annd" to --and--

Column 3, line 19  change "allens" to --a lens--

Column 3, line 23  change "scatter" to --scattered--

Column 3, line 63  change "including" to --included--

Column 4, line 54  change "material" to --materials--

Column 4, line 62  change "Ramam" to --Raman--

Column 6, line 34  change "optimal" to --optical--

Signed and Sealed this

Twentieth Day of September 1977

[SEAL]

Attest:

RUTH C. MASON
Attesting Officer

LUTRELLE F. PARKER
Acting Commissioner of Patents and Trademarks